US 9,478,728 B2

United States Patent
Capobianco et al.

(10) Patent No.: US 9,478,728 B2
(45) Date of Patent: Oct. 25, 2016

(54) PIEZOELECTRIC DEVICES

(71) Applicant: Applied Cavitation, Inc., Goleta, CA (US)

(72) Inventors: Joseph Albert Capobianco, Marlton, NJ (US); Dana Lynn Hankey, Santa Barbara, CA (US); Marshall Campion Tibbetts, Goleta, CA (US); Huidong Li, Richland, WA (US)

(73) Assignee: APPLIED CAVITATION, INC., Goleta, CA (US)

( * ) Notice: Subject to any disclaimer, the term of this patent is extended or adjusted under 35 U.S.C. 154(b) by 0 days.

(21) Appl. No.: 14/655,332

(22) PCT Filed: Dec. 24, 2013

(86) PCT No.: PCT/US2013/077682
§ 371 (c)(1),
(2) Date: Jun. 24, 2015

(87) PCT Pub. No.: WO2014/105898
PCT Pub. Date: Jul. 3, 2014

(65) Prior Publication Data
US 2016/0218272 A1    Jul. 28, 2016

Related U.S. Application Data

(60) Provisional application No. 61/848,048, filed on Dec. 26, 2012.

(51) Int. Cl.
*G01N 27/00* (2006.01)
*H01L 21/00* (2006.01)
(Continued)

(52) U.S. Cl.
CPC ....... *H01L 41/083* (2013.01); *G01N 33/54366* (2013.01); *H01L 41/053* (2013.01); *H01L 41/27* (2013.01); *H01L 41/297* (2013.01)

(58) Field of Classification Search
CPC ...... C40B 60/12; C40B 60/00; G01N 35/00; G01N 15/06; G01N 33/00; G01N 33/48; G01N 27/00; H01L 21/00; H01L 21/20; H01S 4/00

USPC .............. 422/68.1, 82.01, 82.02, 98; 438/48, 438/381, 584; 29/592.1; 506/39, 33; 436/43
See application file for complete search history.

(56) References Cited

U.S. PATENT DOCUMENTS

| 4,845,399 A | * | 7/1989 | Yasuda et al. | 310/366 |
| 5,381,385 A | * | 1/1995 | Greenstein | 367/140 |

(Continued)

FOREIGN PATENT DOCUMENTS

| JP | 2003-282993 A | 10/2003 |
| JP | 2010-060361 A | 3/2010 |

(Continued)

OTHER PUBLICATIONS

Enoksson P et al: "Fluid density sensor based on resonance vibration", Sensors and Actuators A, Elsevier Sequoia S.A., Lausanne, CH, vol. 47, No. 1-3, Mar. 1, 1995, pp. 327-331, XP004310496, ISSN: 0924-4247, DOI: 10.1016/0924-4247 (94) 00915-5 p. 328, paragraph 3-p. 329, paragraph 3; figures 1-3.

(Continued)

*Primary Examiner* — Brian J Sines
(74) *Attorney, Agent, or Firm* — Foley & Lardner LLP; John D. Lanza

(57) ABSTRACT

Piezoelectric devices are provided. A device can include a top electrode, a first piezoelectric layer having an upper surface disposed on a lower surface of the top electrode, a first center electrode having an upper surface disposed on a lower surface of the first piezoelectric layer, an insulating layer having an upper surface disposed on a lower surface of the first center electrode, a second center electrode having an upper surface disposed on a lower surface of the insulating layer, a second piezoelectric layer having an upper surface disposed on a lower surface of the second center electrode, and a bottom electrode having an upper surface disposed on a lower surface of the second piezoelectric layer. The insulating layer can be positioned substantially at a vertical center of the piezoelectric device. The first center electrode can be electrically connected to the second center electrode.

10 Claims, 11 Drawing Sheets

(51) Int. Cl.
*G01N 15/06* (2006.01)
*G01N 33/00* (2006.01)
*H01L 41/083* (2006.01)
*H01L 41/053* (2006.01)
*H01L 41/27* (2013.01)
*H01L 41/297* (2013.01)
*G01N 33/543* (2006.01)

(56) References Cited

U.S. PATENT DOCUMENTS

| | | | | |
|---|---|---|---|---|
| 5,459,371 | A * | 10/1995 | Okawa et al. | 310/363 |
| 6,121,718 | A | 9/2000 | Mohr, III | |
| 7,207,206 | B2 * | 4/2007 | Pinnaduwage et al. | 73/23.2 |
| 7,282,329 | B2 * | 10/2007 | Manalis et al. | 435/6.11 |
| 8,222,047 | B2 | 7/2012 | Duffy et al. | 436/518 |
| 8,501,117 | B1 * | 8/2013 | Bedair et al. | 422/507 |
| 8,796,904 | B2 * | 8/2014 | Burak et al. | 310/320 |
| 8,902,023 | B2 * | 12/2014 | Choy et al. | 333/187 |
| 2004/0038426 | A1 | 2/2004 | Manalis | |
| 2012/0248941 | A1 | 10/2012 | Shirakawa et al. | |

FOREIGN PATENT DOCUMENTS

| | | |
|---|---|---|
| KR | 10-2008-0018012 A | 2/2008 |
| WO | WO-2009/035125 | 3/2009 |

OTHER PUBLICATIONS

Partial Supplementary European Search Report on 13866689.6 dated Dec. 4, 2015.
Extended European Search Report on 13866689.6 dated Mar. 22, 2016.
International Search Report and Written Opinion on PCT/US2013/077682 dated Apr. 23, 2014.
Sader, John E., Energy Dissipation in Microfluidic Beam Resonator, Journal of Fluid Mechanics, May 2010, pp. 1-5.

* cited by examiner

PIEZOELECTRIC DEVICES

RELATED APPLICATIONS

The present application is a U.S. National Stage filing of International Application No. PCT/US2013/077682, filed Dec. 24, 2013, which claims the benefit of and priority to U.S. provisional patent application U.S. Patent Application No. 61/848,048 filed Dec. 26, 2012, the contents of which are incorporated herein by reference in their entireties.

BACKGROUND

Piezoelectricity is an energy conversion manner by which electrical and mechanical energies can be directly converted to each other. When a voltage is applied to a piezoelectric material, the material experiences stress or changes shape. Similarly, when mechanical energy is applied to a piezoelectric material, an electrical voltage is generated across the material. The physical mechanism of piezoelectric behavior is a function of its crystallography, domain and other microstructures.

SUMMARY OF THE INVENTION

Aspects and implementations of the present disclosure are directed to systems and methods related to piezoelectric devices.

At least one aspect is directed to a multilayer piezoelectric device. The device can include a top electrode, a first piezoelectric layer having an upper surface disposed on a lower surface of the top electrode, a first center electrode having an upper surface disposed on a lower surface of the first piezoelectric layer, an insulating layer having an upper surface disposed on a lower surface of the first center electrode, a second center electrode having an upper surface disposed on a lower surface of the insulating layer, a second piezoelectric layer having an upper surface disposed on a lower surface of the second center electrode, and a bottom electrode having an upper surface disposed on a lower surface of the second piezoelectric layer. The insulating layer can be positioned substantially at a vertical center of the piezoelectric device. The first center electrode can be electrically connected to the second center electrode In some implementations, the first top electrode, the first piezoelectric layer, the first center electrode, the insulating layer, the second center electrode, the second piezoelectric layer, and the bottom electrode are fused together at high temperature. In some implementations, the insulating layer is formed from the same material as the first and second piezoelectric layers. the first central electrode is electrically coupled to the second central electrode. In some implementations, the first top electrode is electrically coupled to the bottom electrode. In some implementations, the device can include a second top electrode having a lower surface disposed on an upper surface of the first piezoelectric layer, the second top electrode electrically isolated from the first top electrode. In some implementations, the second top electrode is electrically coupled to one of the first central electrode and the second central electrode.

At least one aspect is directed to a piezoelectric device array. The array can include a first piezoelectric beam and a second piezoelectric beam. Each of the first piezoelectric beam and the second piezoelectric beam can be coupled to a clamp. The first piezoelectric beam and the second piezoelectric beam can extend substantially perpendicular to the clamp. The piezoelectric beams can be configured to oscillate substantially in phase with one another.

In some implementations, a surface of the first piezoelectric beam is substantially in contact with a surface of the second piezoelectric beam when the first and second piezoelectric beams are at rest. In some implementations, the array can include a first proof mass coupled to the first piezoelectric beam and a second proof mass coupled to the second piezoelectric beam, the first and second proof masses selected to enable the first and second piezoelectric beams to oscillate in phase.

At least one aspect is directed to a piezoelectric sensor including a first piezoelectric beam having a first end fixed to a clamp. The first beam can include a channel embedded within the first beam and configured to transport a test fluid. In some implementations, the sensors includes a second piezoelectric beam having second end fixed to the clamp, the second beam comprising a second channel embedded within the second beam and configured to transport the test fluid. In some implementations, the first beam is configured to detect a presence of a first analyte within the test fluid and the second beam is configured to detect a presence of a second analyte, different from the first analyte, within the test fluid. In some implementations, both the first beam and the second beam are configured to detect a presence of a first analyte within the test fluid. In some implementations, a surface of the first piezoelectric beam is substantially in contact with a surface of the second piezoelectric beam when the first and second piezoelectric beams are at rest.

At least one aspect is directed to a method for manufacturing a multilayer piezoelectric device. The method can include forming a lower piezoelectric layer, a middle piezoelectric layer, and an upper piezoelectric layer. The method can include depositing a lower electrode on a lower surface of the lower piezoelectric layer. The method can include depositing a first central electrode on an upper surface of the lower piezoelectric layer. The method can include depositing an upper electrode on an upper surface of the upper piezoelectric layer. The method can include depositing a second central electrode on a lower surface of the upper piezoelectric layer. The method can include positioning a lower surface of the middle piezoelectric layer on an upper surface of the first central electrode. The method can include positioning an upper surface of the middle piezoelectric layer on a lower surface of the second central electrode. The method can include bonding the lower electrode to the first piezoelectric layer, the first piezoelectric layer to the first central electrode, the first central electrode to the middle piezoelectric layer, the middle piezoelectric layer to the second central electrode, and the second central electrode to the upper piezoelectric layer, and the upper electrode.

In some implementations, forming the lower piezoelectric layer, the middle piezoelectric layer, and the upper piezoelectric layer can include preparing a piezoelectric material slurry and tape casting the slurry to form the lower piezoelectric layer, the middle piezoelectric layer, and the upper piezoelectric layer. In some implementations, the method can include sintering the lower piezoelectric layer, the middle piezoelectric layer, and the upper piezoelectric layer. In some implementations, the method can include forming a channel within one of the lower piezoelectric layer, the middle piezoelectric layer, and the upper piezoelectric layer. In some implementations, depositing the lower electrode on the lower surface of the lower piezoelectric layer further comprises screen printing a conductive material onto the lower surface of the lower piezoelectric layer.

These and other aspects and embodiments are discussed in detail below. The foregoing information and the following detailed description include illustrative examples of various aspects and embodiments, and provide an overview or framework for understanding the nature and character of the claimed aspects and embodiments. The drawings provide illustration and a further understanding of the various aspects and embodiments, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

DESCRIPTION OF CERTAIN ILLUSTRATIVE IMPLEMENTATIONS

Following below are more detailed descriptions of various concepts related to, and implementations of, piezoelectric devices. The various concepts introduced above and discussed in greater detail below may be implemented in any of numerous ways, as the described concepts are not limited to any particular manner of implementation. Examples of specific implementations and applications are provided primarily for illustrative purposes.

Energy harvesting refers to the transformation of ambient, free power from the environment into a useable form, most commonly electricity. With such a definition, large scale stationary power plants such as windmills, hydroelectric, solar and geothermal power can be considered energy harvesting. A more focused definition of energy harvesting, is concerned with the capture of ambient power local to an individual person or small piece of equipment.

Piezoelectric energy harvesting devices can include, but are not limited to: single layer bulk piezoelectric devices designed to harvest energy as a result of pure compression of the device; multilayer bulk piezoelectric devices designed to harvest energy as a result of pure compression of the device; multilayer devices consisting of one piezoelectric layer bonded to one non-piezoelectric layer such that bending of the device will induce a longitudinal stress in the piezoelectric layer; multilayer devices consisting of a plurality of piezoelectric layers such that bending of the device will induce longitudinal stresses in multiple piezoelectric layers simultaneously.

Important performance parameters pertaining to a piezoelectric actuator include displacement and blocked force. Simple expansion and contraction displacement is measured as the amount of upward, downward or sideways displacement of a surface of the device. Bending displacement can be measured, for example, at the extreme end away from a clamp in the case of a simple cantilevered beam. In the case of a three-point bending test, upward displacement can be measured at the center of the beam when beam is supported below at the outermost extremities of its length. In the case of a piezoelectric disc actuator, the upward free displacement is measured at the center of the disc with the perimeter of the disc supported from below. Blocked force is defined as the maximum amount of force that can be supported or moved in a non-negative direction by a piezoelectric actuator with voltage applied across the electrodes of its piezoelectric layers(s).

Figure 1A:
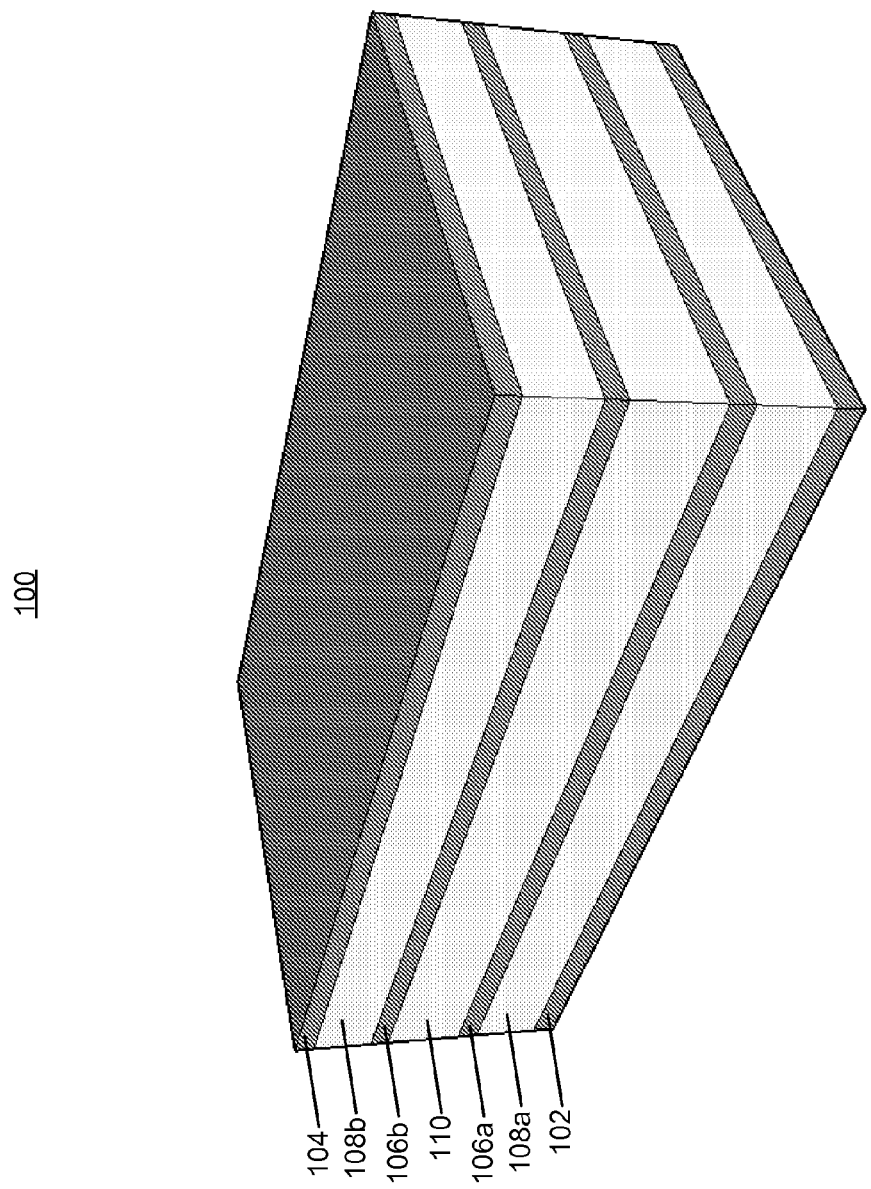
FIGS. 1A-1D show perspective views of various illustrative multilayer piezoelectric devices.

FIGS. 1A-1D show perspective views of various illustrative multilayer piezoelectric devices. The piezoelectric device 100 shown in FIG. 1A is formed from several layers of material. The device 100 includes a bottom electrode 102, a top electrode 104, and two middle electrodes 106a and 106b (generally referred to as middle electrodes 106). The middle electrodes 106 are separated from the bottom electrode 102 and the top electrode 104, respectively, by piezoelectric layers 108a and 108b (generally referred to as piezoelectric layers 108). An insulating layer 110 is positioned between the two middle electrodes 106. While the device 100 is shown in FIG. 1A as a rectangular beam, other form factors may be used. For example, the device 100 could have a cubic or cylindrical shape.

Adjacent layers of the piezoelectric device 100 can be bonded together using glue, epoxy, or other adhesives. In some implementations, the layers may be subjected to high temperatures to fuse the layers together chemically or physically. In operation, the piezoelectric device 100 can change shape upon application of a voltage across the electrodes 102, 104, and 106. For example, application of a voltage can cause the piezoelectric layers 108 to expand or contract. This behavior is known as the converse piezoelectric effect. Such expansion or contraction can be used to apply force to another object brought in contact with the device 100. When a force, pressure, or stress is applied to the piezoelectric layers 108, an electrical voltage can be generated across the electrodes 102, 104, and 106. This behavior is known as the direct piezoelectric effect.

In some implementations, the relative dimensions of the layers of the device 100 can be selected to improve the maximum displacement and blocked force achievable by the device 100. For example, the total thickness of the two middle electrodes 106 and the insulating layer 110 can be increased, and the thickness of the piezoelectric layers 108 can be decreased. The decrease in thickness of the piezoelectric layers 108 can lead to an increase in electric field within each piezoelectric layer 108 at a given voltage. Electric field is defined as an electric voltage potential divided by distance over which it operates. Furthermore, the stress and strain of the piezoelectric layers 108 act over a range of positions farther from the central horizontal plane of the device 100 when the thickness of the insulating layer 110 is increased. As such, the effect of the contractions and expansions of the piezoelectric layers 108 can lead to more bending of the device. When the device 100 is used in such a manner for energy harvesting, more power is generated as a result of increased strain in a thinner piezoelectric layers 108.

In some implementations, the dimensions of the layers may be altered based on the stiffness of the layers and the overall stiffness of the device 100. For example, if the elastic modulus of the middle electrodes 106 and insulating layer 110 is substantially equal to the elastic modulus of the piezoelectric layers 108, then the increased thickness of the middle electrodes 106 and insulating layer 110 should be reflected as half as much of a reduction in thickness of the top piezoelectric layer 108b as well as half as much reduction in thickness of the bottom piezoelectric layer 108a, such that the total thickness of the device remains unchanged. If the elastic modulus of the middle electrodes 106 and insulating layer 110 differ from the elastic modulus of the piezoelectric layers 108, then the increase in thickness of the middle electrodes 106 and insulating layer 110 must be counteracted by decreasing the thicknesses of the piezoelectric layers 108 such that the stiffness of the entire device 100 remains constant. In this case, the thickness of the final device 100 may differ from that of the original.

In some implementations, the middle electrodes 106 and insulating layer 110 may be replaced with a single central electrode. However, to achieve the same thickness using a single central electrode can require more electrode material and complicated bonding processes. In some implementations, the introduction of the insulating layer 110 between the middle electrodes 106 can overcome these problems by reducing the amount of electrode material required to achieve a given thickness.

The purpose of the insulating layer 110 is to move the middle electrodes 106 away from the central horizontal plane of the device 100, so as to achieve the performance enhancements discussed above. In some implementations, the insulating layer 110 can be engineered to be of the same coefficient of thermal expansion as the piezoelectric layers 108 so as to minimize or negate the problems resulting from shrinkage mismatch between layers of the device. Furthermore, to facilitate manufacture, the insulating layer 110 can be of the exact same material as the piezoelectric layers 108.

In some implementations, the piezoelectric layers 108 can be formed from any ferroelectric or ferromagnetic material. For example, the piezoelectric layers 108 may include leaded ceramics such as lead-zirconate-titanate (PZT) and lead magnesium niobate-lead titanate (PMN-PT). In other implementations, the piezoelectric layers 108 can be formed from lead free ceramics, such as lithium niobate and barium titanate. In still other implementations, the piezoelectric layers can be formed from piezoelectric polymers or conductor filled polymers.

In some implementations, the lower electrode 102, upper electrode 104, and middle electrodes 106 may be formed from a conductive material such as platinum or siler-palladium. For example, these conductors may be co-sintered with PZT piezoelectric layers 108 at a temperature in the range of about 1000 degrees Celsius to about 1400 degrees Celsius. Silver or gold may also be used for the lower electrode 102, upper electrode 104, and middle electrodes 106. In some implementations, the lower electrode 102, upper electrode 104, and middle electrodes 106 can be formed from base metals such as nickel, copper, and tungsten. In still other implementations, the lower electrode 102, upper electrode 104, and middle electrodes 106 can be formed from conductive ceramic materials.

Figure 1B:
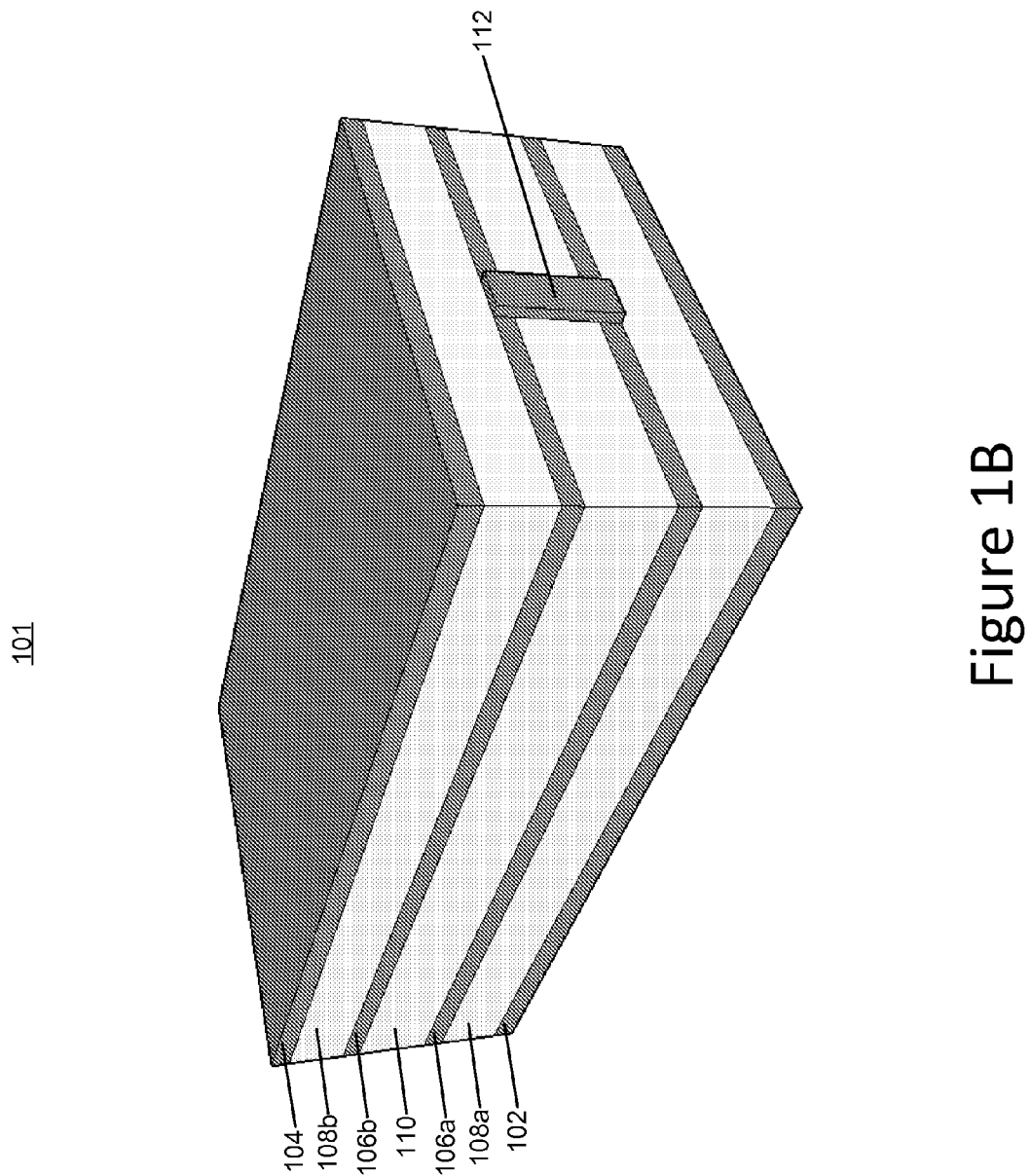

The two middle electrodes 106 must be maintained at the same voltage potential during use of the device 100. This can be accomplished by connecting the two middle electrodes 106 electrically. A further advantage of electrically connecting or 'shorting' the middle electrodes 106 is that no additional electrical connections to the new electrode layer are required during use of the device 100. In some implementations, the middle electrodes 106 can be shorted by applying a conductive material along a face of the device 100 between the middle electrodes 106. For example, FIG. 1B shows conductive material 112 coupling the middle electrode 106a to the middle electrode 106b in a device 101 similar to the device 100. In some implementations, the conductive material 112 may be formed from the same material used to form the middle electrodes 106. The conductive material 112 can be deposited after deposition of the other layers of the device 101. Because the insulating layer 110 does not conduct electricity, the conductive material 112 can be placed in direct contact with the insulating layer 110 without negatively impacting the performance of the device 101.

Figure 1C:
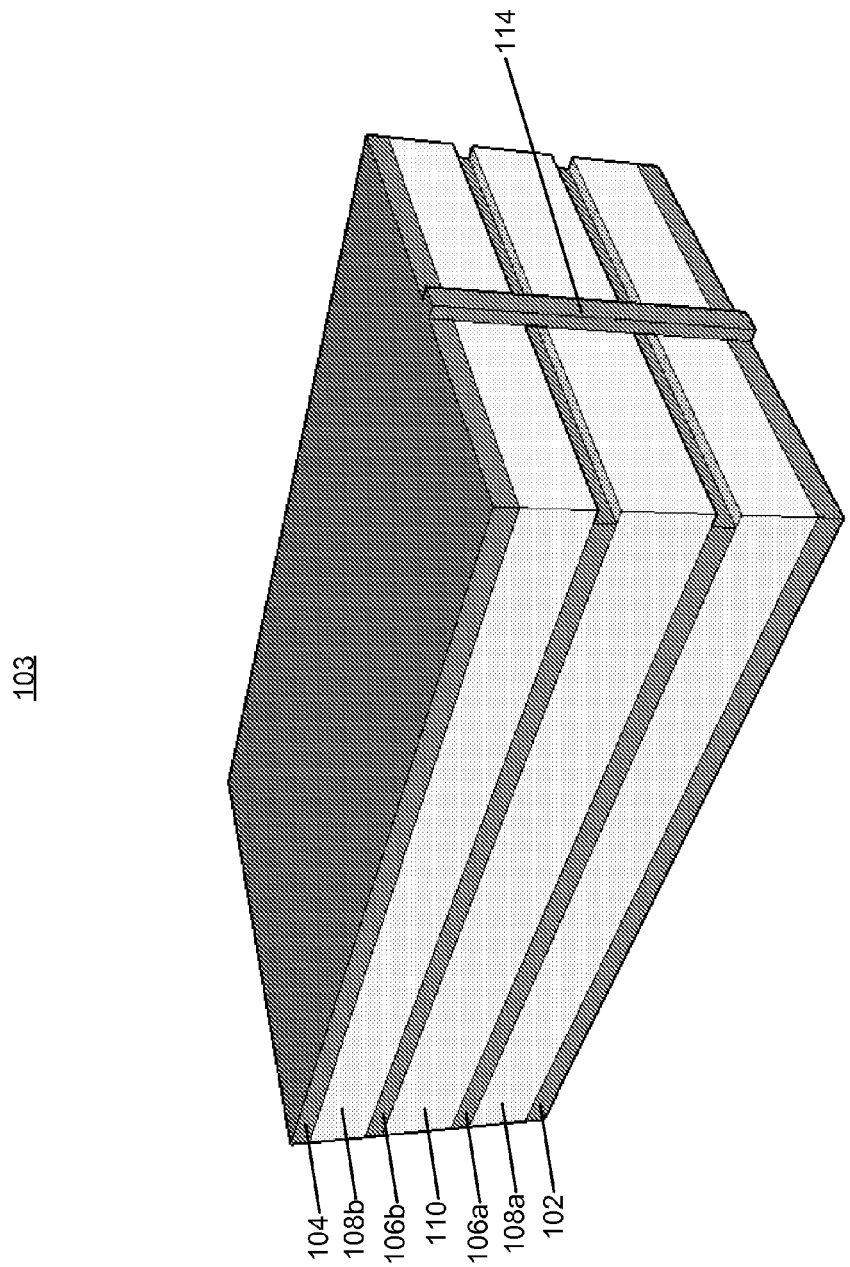

The device 101 shown in FIG. 1B requires three electrical connections—one to the bottom electrode 102, one to the top electrode 104, and one to the middle electrodes 106. In some implementations, the need for separate electrical connections to the bottom electrode 102 and the top electrode 104 can be eliminated. For example, FIG. 1C shows a device 103 in which the conductive material 114 is used to electrically couple the bottom electrode 103 and the top electrode 104. The conductive material is applied to a face of the device 103. To avoid erroneously coupling the middle electrodes 106 to either the bottom electrode 102 or the top electrode 104, the middle electrodes 106 can be recessed relative to the piezoelectric layers 108 and insulating layer 110, as shown in FIG. 1C.

Figure 1D:
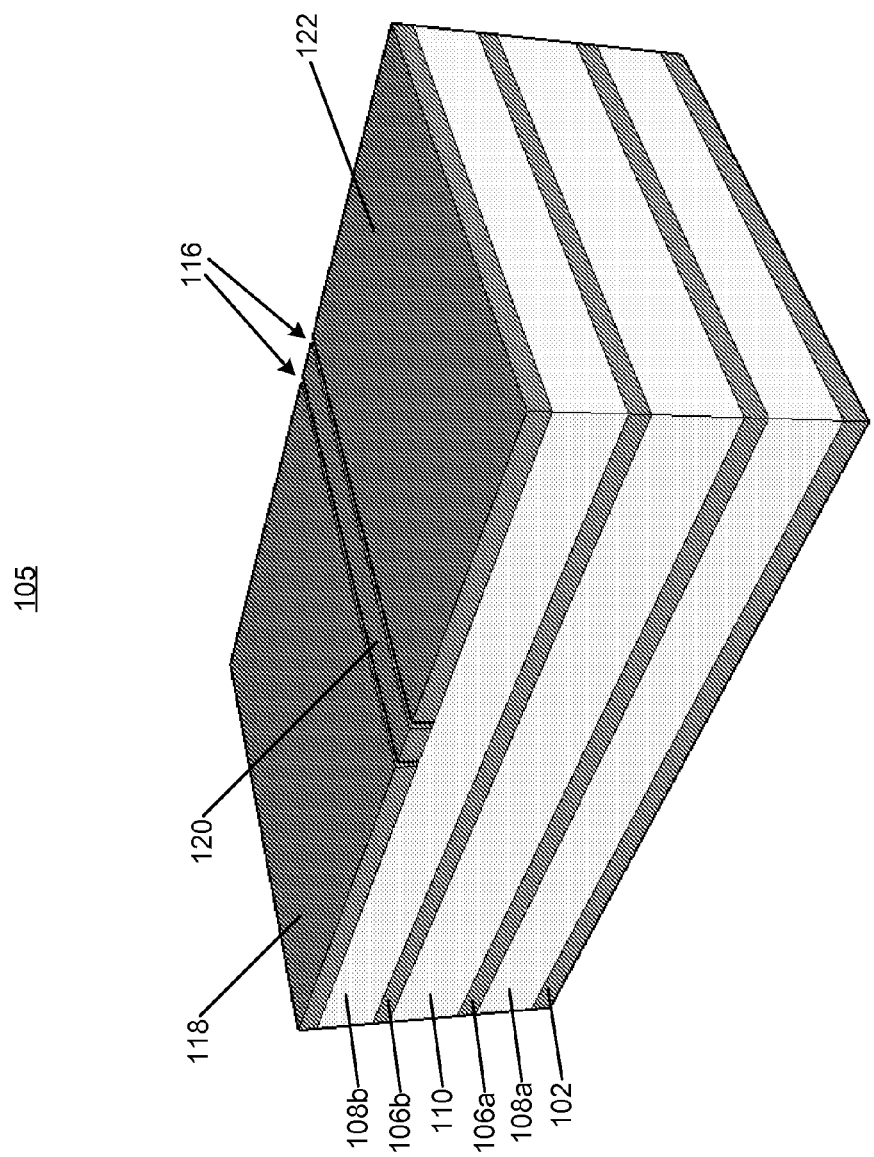

FIG. 1D shows a multilayer piezoelectric device 105 that is designed to further ease electrical connection to the device. The device 105 includes a bottom electrode 102, and two middle electrodes 106a and 106b (generally referred to as middle electrodes 106). The middle electrodes 106 are separated from the bottom electrode 102 and a top layer, respectively, by piezoelectric layers 108a and 108b (generally referred to as piezoelectric layers 108). An insulating layer 110 is positioned between the two middle electrodes 106. In addition, the device 105 includes two gaps 116 in the top layer, which define three separate electrodes 118, 120, and 122.

In some implementations, the device 105 may be very thin, making it difficult to form electrical connections with various layers of the device 105. During fabrication, electrical connections may be formed between the middle electrodes 106 or the bottom electrode 102 and any of the electrode regions 118, 120, and 122. A user of the device therefore can electrically connect to only the upper regions 118, 120, and 122 of the device 105 to apply voltages to the various layers. Connections between upper regions 118, 120, and 122 may be formed in various ways, including by depositing conductive material along a face of the device 105, as described above in connection with FIGS. 1B and 1C. In other implementations, connections may be formed through the center of the device 105. The gaps 116 may be formed, for example, by an etching process used to remove material from the top layer of the device 105.

Figure 2A:
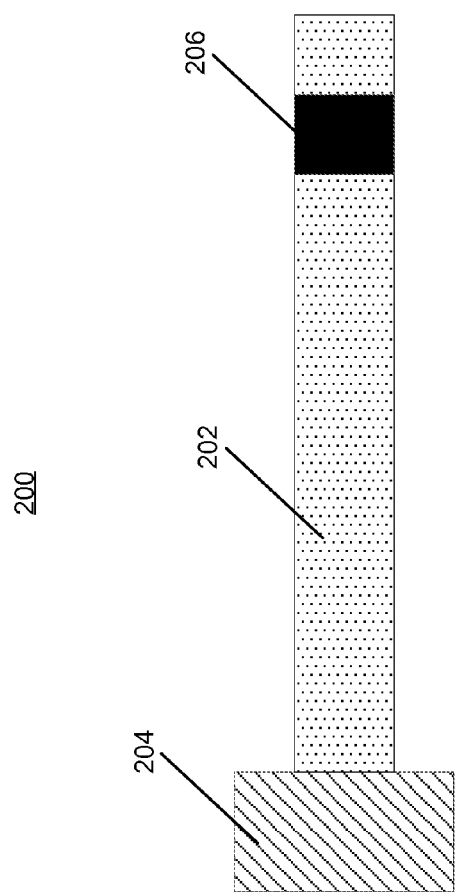
FIG. 2A shows a side view of a piezoelectric cantilever assembly, according to an illustrative implementation.

FIG. 2A shows a side view of a piezoelectric cantilever assembly 200, according to an illustrative implementation. The assembly 200 includes a beam 202 rigidly fixed at its left-hand end to a clamp 204. A proof mass 206 is fixed to the right-hand side of the beam 202. Deflection of the beam 202, for example due to forces in the surrounding environment, can generate a voltage, as discussed above. In this way, the assembly 200 can be used to harvest energy from the environment.

When the beam 202 deflects, oscillates, or resonates, its right-hand end will deflect in the upward and downward directions within the plane of the page. In addition to the thickness of the beam 202, and the thickness of any mass 206 used, this upward and downward deflection must be factored into the calculation of the 'working volume' of the device. The working volume, $V_w$, of the device can be defined as:

$$V_w = (t_b + t_m + d_d + d_u)lw + V_c$$

where tb is the thickness of the beam 22, tm is the thickness of the mass, if any, du is the maximum upward displacement of the beam in deflection, oscillation or resonance, dd is the maximum downward displacement of the beam in deflection, oscillation or resonance, l is the length of the beam, w is the width of the beam and Vc is the volume of the clamp.

If a two or more similar freely displacing, oscillating or resonating assemblies 200 were to be placed as closely together as possible, the center planes (orthogonal or normal to the thickness direction of the beams 202) of two adjacent beams 202 must necessarily be placed at least $(t_b + t_m + d_u + d_d)$ apart. This spacing will allow for the plurality of beams 202 to deflect, oscillate or resonate freely, without any chance of colliding with each other. As such, the total working volume of such a stack of beams would be:

$$V_w = n(t_b + t_m + d_d + d_u)lw + V_c$$

where n is the number of beams in the stack. However, in some implementations, the minimum spacing can be reduced by guaranteeing that all beams 200 in the stack would deflect, oscillate or resonate perfectly 'in phase' with each other. That is, all beams 200 would deflect identically upward together and all beams 200 would deflect downward identically. In some implementations, this identical, completely in-phase oscillation can be made to occur by constructing all beams 200 in the assembly so that they have identical bending moduli, where bending modulus is the parameter taking into effect the geometry of the beam 200 as well as the elastic moduli of all the layers in the beam 200. If such a plurality of identical beams 200 were produced and stacked closely together, the center plane of two adjacent beams 200 could theoretically be placed as close as (tb+tm). Thus, the total working volume of such a stack of beams would be:

$$V_w = (n(t_b + t_m) + d_d + d_u)lw + V_c$$

Thus, comparing a stack of in-phase beams to a stack of out of phase beams, the total working volume of the device is decreased by the amount:

$$\Delta V = (n-1)(d_d + d_u)lw$$

This same principle applies to the condition of a deflecting, oscillating or resonating beam, supported on both ends and achieving maximum deflection at the center point of its length. These examples are discussed further below in connection with FIGS. 2B and 2C.

In some implementations, the assembly 200 can be used as an actuator. A voltage can be applied to the assembly 200. As a result of the applied voltage, the beam 202 can change shape. Because one end of the beam 202 is fixed to the clamp 204, the change in the shape of the beam 202 can cause the free end of the beam to actuate upwards or downwards. There are several potential applications for the assembly 200 configured as an actuator.

For example, one or more instances of the assembly 200 can be configured to provide tactile feedback to a user of a handheld electronic device. The assembly 200 can be embedded in a flexible surface of the handheld electronic device. The assembly 200 can be configured to receive an applied voltage and can actuate the free end of the beam 202 against the surface, cause the surface to deform slightly. The surface can be a surface held by the user during use of the device, so that the user is able to feel the deformation of the surface that occurs when the beam 202 is actuated. A controller can be configured to apply the actuation voltage to the assembly 200 in order to provide an alert to the user via tactile feedback, for example.

In some implementations, the assembly 200 can be used as a microfluidic pump. For example, the assembly 200 can be embedded within a microfluidic channel configured to transport fluid. The assembly 200 can be aligned such that actuation of the beam 202 causes the beam 202 to move within the channel substantially in the direction of fluid flow. Actuation of the beam 202 can therefore be used to increase pressure within the microfluidic channel, driving fluid through the channel upon application of an actuation voltage.

In another example, the assembly 200 can be embedded within a microfluidic channel to implement a microfluidic valve. The assembly 200 can be oriented within the channel such that, in an unactuated state, the beam 202 obstructs fluid flow within the channel. Actuation of the beam 202 can move the beam out of the channel, increasing the cross-sectional diameter of the channel and allowing more fluid to flow. Therefore, to open the microfluidic valve, a voltage can be applied to the assembly 200 to actuate the beam 202. To close the valve, the voltage can be removed, allowing the beam 202 to obstruct fluid flow by returning to its unactuated state. The microfluidic pumps and valves described herein can be used to implement drug delivery devices, fuel injectors, or ink jet printers, for example.

In other implementations, the assembly 200 can be used as an actuator to precisely control the position of optical equipment. For example, the assembly 200 can be used to control the position of microscope stages. An actuation voltage can be applied to the assembly 200, causing the beam 202 to actuate upwards or downwards. The beam 202 can be configured to perpendicular to a focal plane of the microscope. The beam 202 can be mechanically coupled to the microscope stages and can be actuated to adjust the focal plane of the microscope by driving one or more microscope stages into a desired position.

Figure 2B:
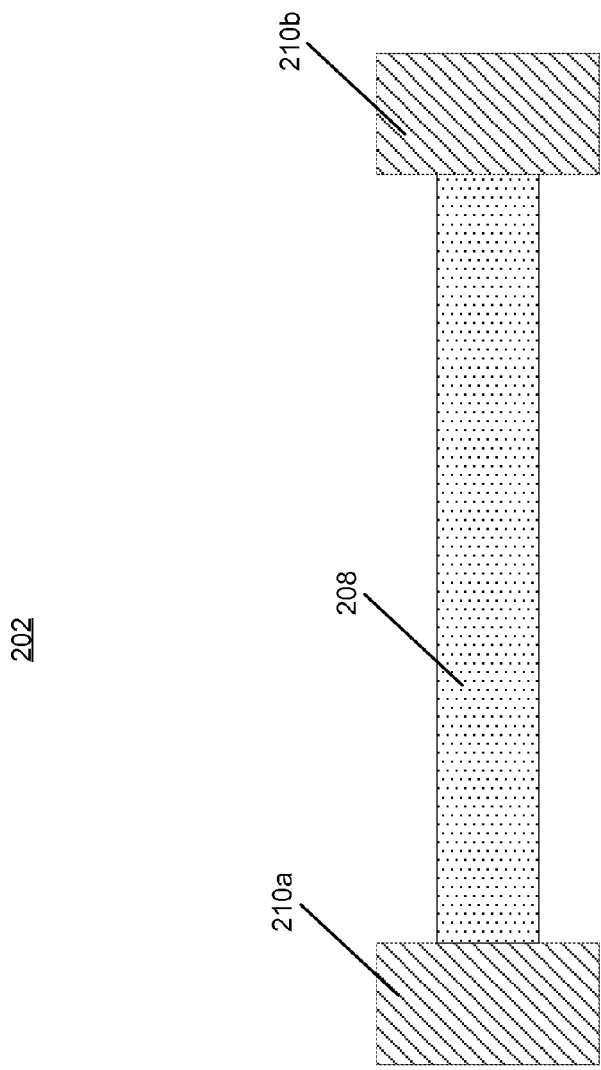
FIG. 2B shows a side of a piezoelectric beam assembly, according to an illustrative implementation.

FIG. 2B shows a side of a piezoelectric beam assembly 201, according to an illustrative implementation. The assembly 201 includes a beam 208 supported by two clamps 210a and 210b (generally referred to as clamps 210). As with the case of a cantilevered assembly 200, in some implementations this three-point bending beam assembly 201 can also be tuned by a proof mass, although a proof mass is not shown in FIG. 2B. Deflection of the piezoelectric beam 208 can generate a an electrical voltage. For example, a downward or upward force applied to the central portion of the beam 208 can cause the beam 208 to bend. In some implementations, the assembly 200 can bend to due environmental disturbances and can therefore harvest energy from its environment. The assembly 201 is subject to the same spacing requirements discussed above in connection with FIG. 2A. The minimum spacing can similarly be reduced by guaranteeing that two adjacent assemblies will oscillate phase with each other.

Figure 2C:
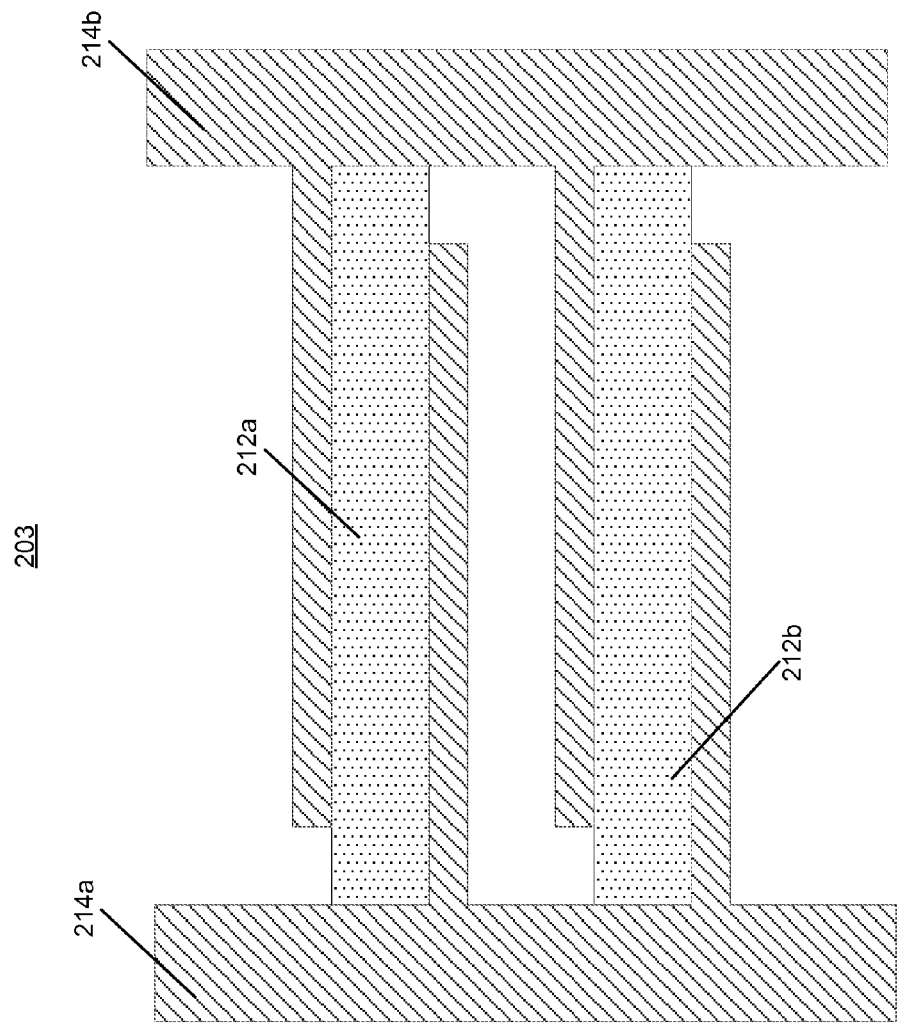
FIG. 2C shows a side view of an array assembly including two piezoelectric beams, according to an illustrative implementation.

FIG. 2C shows a side view of an array assembly 203 including two piezoelectric beams 212a and 212b (generally referred to as beams 212), according to an illustrative implementation. Each beam 212a is fixed at both ends to electrodes 214a and 214b. The beams 212 can deflect downward or upward within the plane of the page. In some implementations, the spacing between the beams 212 in the assembly 203 can be selected to be as small as possible. For example, the beams 212 can be designed to have substantially identical bending characteristics, such as their physical dimensions and bending moduli. By guaranteeing that the beams 212 will oscillate substantially in phase, the beams 212 can be stacked closer together in the array assembly 203, relative to beams having different phases of oscillation.

In some implementations, the beams 212 of the array assembly 203 may be constructed in layers, with sacrificial material separating the beams 212 during manufacturing. For example, the amount of sacrificial material between the beams 212 could be selected based on the desired spacing of the beams 212 in the final product. In some implementations, the sacrificial material can be removed at the end of the manufacturing process to leave a gap, allowing the beams 212 to oscillate. In some implementations, the sacrificial material can be a carbon-based compound. For example, the sacrificial material can include polysaccharides, acrylics, vinyls, polycarbonates, polyamides, or polyimides.

Reducing the spacing between the beams 212 increases the power density of the array assembly 203. In some implementations, the array assembly 203 may include any number of beams 212, and all of the beams may be designed to oscillate in phase. As a result, the array assembly 203 can achieve a high degree of power density. To further increase power density, the beams 212 may be designed as multilayer piezoelectric devices with any of the performance enhancing features described above in connection with FIGS. 1A-1D.

As discussed above, the array 203 may be used as an energy harvesting device. Forces applied to the beams 212 can cause the beams 212 to deform, which generates an electrical potential across the electrodes 214. The electrical energy can be used to power an electric device or can be stored in a storage device, such as a capacitor or a rechargeable battery.

In some implementations, the array 203 can be used to harvest wind energy. For example, the array 203 can be located in an outdoor area that typically experiences high wind speeds. The array 203 may be coupled to another device configured to direct the energy of the wind to apply a force to the beams 212. In some implementations, the array 203 may be coupled to a windmill blade or to another device having a large surface area positioned normal to the force of the wind. The windmill blade or other device can be configured to apply a force to the beams 212 in response to wind forces. The force applied to the beams 212 can cause the beams 212 to deform, generating an electrical voltage across the electrodes 214. The generated voltage can then be used to power an electrical device.

In some implementations, the array 203 can harvest energy from water. In one example, the array 203 can be located in a river or stream, and can harvest the kinetic energy of the flowing water. The beams 212 of the array 203 can be coupled to a paddle or propeller configured to extract energy from the flowing water. For example, the paddle or propeller can be configured to apply a force to the beams 212, causing the beams to deform and generate a voltage across the electrodes 214.

In some implementations, the array 203 can harvest vibrational energy. For example, the array 203 can be mounted to or placed in contact with a pump, generator, or other device that typically experiences vibrational forces. The vibration of such devices typically represents mechanical energy that is lost to the environment, as the vibrations do not serve a functional purpose within these devices. Therefore, using the array 203 to capture the vibrational energy can improve the energy efficiency of these systems. The vibration of a device to which the array 203 is mounted can cause the beams 212 to deform periodically, thereby generating a voltage across the electrodes 214. In some implementations, the beams 212 can be configured to have a resonant frequency substantially equal to the resonant frequency of the vibrational device to which the array 203 is mounted. Such a configuration can increase the amount of vibrational energy converted to electrical energy by the array 203. In some implementations, the energy harvested by the array 203 may be reintroduced into the vibrational device. For example, the vibrational device can have a battery coupled to the electrodes 214. This technique can help to reduce the energy loss in vibrational systems.

In some implementations, the array 203 can be used as a motion activated switch. Because the an electrical voltage is generated across the electrodes 214 in response to a force applied to the beams 212, the absence of an electrical voltage can indicate that no force is applied to the beams 212. The array 203 can therefore be used as a switch in applications in which motion (i.e., acceleration) is intermittent. For example, the array 203 can be fixed to a handheld electronic device, such as portable computer, game controller, remote control, or medical device. The array 203 can serve as a portion of a sensor to determine when the device is in use. The electrodes 214 of the array 203 can be coupled to a switch configured to apply power to the electronic device when the device is in use. The switch can be configured to detect a presence or absence of a voltage across the electrodes 214. When a user picks up the handheld electronic device, the device (along with the array 203 fixed to the device) experiences acceleration. The beams 212 can deform due to the forces applied by the user picking up the device, resulting in a voltage across the electrodes 214. The switch can detect the voltage, and can turn on the electronic device as the user picks up the device. While the handheld electronic device is in use, the beams 212 will frequently be under stress due to the movement of the device in the user's hands, and therefore a voltage will frequently be present across the electrodes 214. The switch can detect the voltage and determine that the device is in use while the voltage is present. The switch can therefore be configured to allow power to be applied to the device while the device is in use. When the switch no longer detects a voltage across the electrodes 214, indicating that the device is at rest and is no longer in use, the switch can turn off power to the device. The array 203 can be used in this way to conserve power by working with a switch to turn off power to a device when the device is not in use.

Similarly, the array 203 can be incorporated into a sensor mounted to shipping crate. The sensor can be configured to measure environmental parameters such as temperature, humidity, or location and can transmit the measured values to a remote server to provide a method for tracking the shipping container. The array 203 can be used to determine when the shipping crate is moving. For example, when the shipping crate is moved from a resting position, it will experience forces that can cause deformation of the beams 212 of the array 203 mounted to the crate. As a result, a voltage will be present across the electrodes 214 when the shipping crate is moved and will not be present when the shipping crate is at rest. In some implementations, the array 203 can be coupled to a switch configured to apply power to a transmitter coupled to the sensor. For example, the switch could detect movement of the crate by measuring a voltage across the electrodes 214. The switch could then apply power to the transmitter only when the container is in motion and could remove power when the crate is at rest in order to save energy.

Figure 3A:
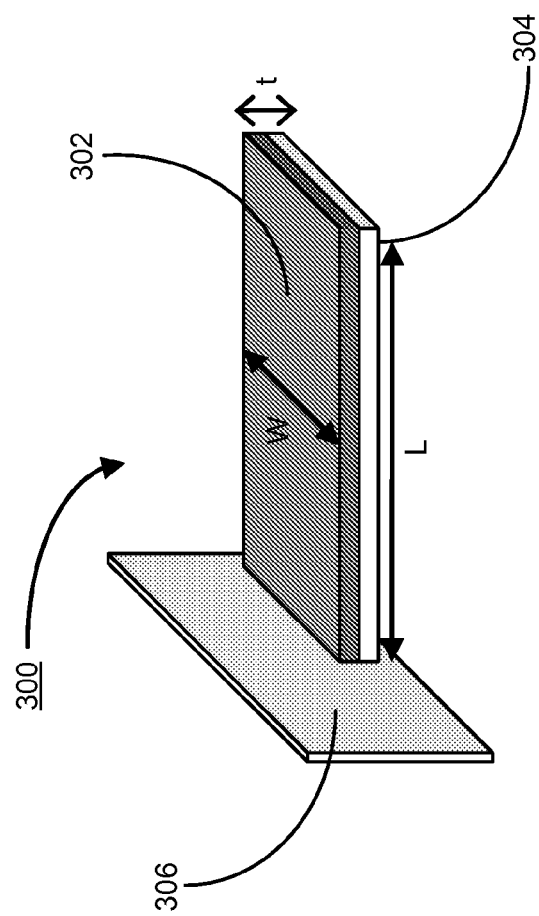
FIG. 3A shows a perspective view of a piezoelectric cantilever sensor, according to an illustrative implementation.

FIG. 3A shows a perspective view of a piezoelectric cantilever sensor 300, according to an illustrative implementation. The sensor 300 includes a piezoelectric layer 302 bonded to a non-piezoelectric layer 304. In some implementations, the non-piezoelectric layer 304 can be formed from glass, copper, tin, or nickel. One end of the piezoelectric layer 302 and non-piezoelectric layer 302 is fixed to a clamp 306, while the other end is permitted to move freely.

When a voltage is applied to the thickness direction of the piezoelectric layer 302, it will elongate or shrink along the length and width directions depending on the polarity of the field. However, the non-piezoelectric layer 304 does not deform and constrains the movement of the piezoelectric layer 302 and resulting in the alternative bending (i.e., vibration under alternating current) of the sensor 300. The resonance frequency of the sensor 300 can be measured by electrical means.

An impedance analyzer is used to measure phase angle ($\theta$) versus frequency spectrum, where $\theta=\tan^{-1}(\text{Im}(Z)/\text{Re}(Z))$ is the phase angle of the complex electrical impedance, Z, and Im(Z) and Re(Z) are the imaginary and real part of the electrical impedance. Off resonance, the sensor 300 behaves as a capacitor with a phase angle close to $-90°$. At or near resonance, the in phase induced voltage from the strain induced by vibration will gave rise to a peak in the real part Re(Z) of the electrical impedance, and hence a peak in the phase angle. At or near resonance, the in phase induced voltage from the strain induced by vibration will create a peak in the phase angle.

The sensor 300, can be considered as a thin beam in flexural vibration with one end fixed and the other end free. Important parameters for protein detection are discussed further below. In the x-y plane, with x as the longitudinal axis and y as the transverse axis of the thin beam, the natural transverse vibration of thin beam was governed by the Bernoulli-Euler equation:

$$D\frac{\partial^4 z}{\partial x^4} + m_1 \frac{\partial^2 z}{\partial t^2} = 0$$

where the bending modulus (D) and mass per unit length (ml) are independent of the position (uniform beam). Using the general solution of the Bernoulli-Euler equation:

$$z(x,t)=[C_1 \sin(kx)+C_2 \cos(kx)+C_3 \sin h(kx)+C_4 \cos h(kx)]e^{i\omega t}$$

and the boundary conditions of the piezoelectric cantilever sensor can be determined. One end is clamped and cannot vibrate, therefore:

$$\begin{cases} z = 0, \\ \frac{dz}{dx} = 0, \end{cases} @x = 0$$

The other end is free, and therefore:

$$\begin{cases} D\frac{d^2 z}{dx^2} = 0, \\ D\frac{d^3 z}{dx^3} = 0, \end{cases} @x = 1$$

the wave vector (wave number):

$$k^4 = \omega^2 \frac{m}{D}$$

can be deduced numerically. Using this wave factor, the resonant frequency of the sensor 300 of length, L, and width, w, consisting of a piezoelectric layer of thickness tp, density, pp, and Young's modulus Yp, and a non-piezoelectric layer of thickness tn, density, pn, and Young's modulus Yn can be deduced to be:

$$f_n = \frac{v_n^2}{2\pi} \frac{1}{L^2} \sqrt{\frac{D_p}{m}}$$

$$Dp = \frac{Y_p^2 t_p^4 + Y_n^2 t_n^4 + 2Y_p Y_n t_p t_n (2t_p^2 + 2t_n^2 + 3t_p t_n)}{12(Y_p t_p + Y_n t_n)}$$

$$m = \rho_p t_p + \rho_n t_n$$

where $D_p$ is the bending modulus per unit width, m is the mass per unit area and $v_2$ is the dimensionless nth mode eigenvalue, which are defined by the product of the wave factor times the length. The bending modulus per unit width can be rewritten:

$$Dp = \frac{Y_{eff} t^3}{12}$$

$$Y_{eff} = \frac{Y_p^s r_p^4 + Y_n^s r_n^4 + 2Y_p Y_n r_p r_n (2r_p^2 + 2r_n^3 + 3r_p r_n)}{(Y_p r_p + Y_n r_n)}$$

$$r_p = \frac{t_p}{t}; r_n = \frac{t_n}{t}$$

Using this form of the mathematical relationship it can be shown that the effective Young's modulus $Y_{eff}$ of the sensor 300 depends only upon the Young's modulus of the materials and the dimensionless thickness fractions. Furthermore, the mass per unit area can be rewritten as:

$$m = t\rho_{eff}$$

$$\rho_{eff} = \rho_p r_p + \rho_n r_n$$

Using these revisions of the mass per unit area, and bending modulus per width, the resonant frequency of the cantilever can be expressed in the more conventional form:

$$f_n = \frac{v_R^s}{2\pi\sqrt{12}} \frac{t}{L^2} \sqrt{\frac{Y_{eff}}{\rho_{eff}}}$$

The resonance frequency can change due to mass loading, and adsorption induced differential surface stress. The surface stress can affect the spring constant and resonant frequency can be expressed using the relationship:

$$f'_n = \frac{v'^2_n}{2\pi}\sqrt{\frac{K + \Delta K}{M_e + \Delta m}}$$

where fn' is the frequency and ΔK is the change in spring constant due to adsorption induced surface stress. The surface stress will induce an axial force, N, and a moment, M, $$N = \int_0^L s \, dl = sl$$

$$M = \frac{sit}{2}$$

which is a force acting along the median plane of the sensor 300. In the equation s represents the stress per unit length, l represents length and t thickness. The stress per unit length, s is equal to the sum of the acting stresses on the cantilever (s=s1+s2), where s1 is acting on the top surface and s2 is acting on the bottom surface. Tensile or compressive force of the cantilever is determined by the sign of the resultant surface stresses s1 and s2. The resonant frequency is deduced by first considering the axial force in the Bernoulli-Euler equation $$D\frac{\partial^4 z}{\partial x^2} - N\frac{\partial^2 z}{\partial x^2} + m_l\frac{\partial^2 z}{\partial t^2} = 0$$

assuming that the axial force due to the surface stress should be constant and act at the free end of the caused by the surface stress for the effective rigidity of the cantilever and neglects the bending rigidity of the cantilever. [6] For this model, the governing equation for a taut string can be written as:

$$N\frac{\partial^2 z}{\partial x^2} + m_l\frac{\partial^2 z}{\partial t^2} = 0$$

and from this the resonant frequency can be deduced:

$$f = \frac{1}{4l}\sqrt{\frac{N}{n_g m_l}} = \frac{1}{4}\sqrt{\frac{s_1 + z_2}{n_g m_b}}$$

where the fundamental mode transverse wave length, 4l, ng is the geometrical coefficient for different shapes of cantilevers, ml is the mass per unit length and mb is the mass of the cantilever beam. In general, the whole sensor 300 can also be treated as an effective mass connected in parallel to two springs with K contributed by bulk property and Ks contributed by the surface stress. The change in spring constant due to the surface adsorption is given by:

$$\Delta K = \frac{\pi^2 \frac{M_e}{m_b}}{4 n_g}(\delta s_1 - \delta s_2)$$

where δs is the change in surface stress before and after adsorption. When ΔM<<mb and ΔK<<K the resonant frequency after adsorption can be approximated to be:

$$f_2 = f_1\left[1 + \frac{1}{2}\left(\frac{\Delta K}{K} - \frac{\Delta M}{M_e}\right)\right]$$

In biosensing applications, the devices must be electrically insulated in a manner that allows them to be completely submerged in aqueous ionic buffers without a short circuit. The devices also must be submerged in an external reservoir, containing the analyte to be detected. In some implementations, the external reservoir is a flow cell in which the solution is recirculated under conditions selected to facilitate antigen detection. In some implementations, the sensor 300 is positioned along the center line of the channel, and oriented with the faces tangential to the flow. The principle of using the flow cell is to bring the antigens in contact with the sensor 300 in a manner that can increase the selectivity and sensitivity, and reduce the time required for detection. This is achieved by maintaining laminar flow. When the calculated Reynolds Number (Re) for a particular system is less than about 2000, the fluid flow is termed 'laminar,' while when the Re exceeds about 2000, the flow is termed 'turbulent. Laminar flow is a type of fluid flow where the fluid in motion is characterized by adjacent layers that share common velocities and pressures. In laminar flow the properties of fluid velocity and pressure vary continuously as one moves from the wall of the flow, through the center of the channel and to the far wall. As such, mathematical equations can be derived to predict the fluid flow properties at given points in space based on the fluid's physical properties, volumetric flow rate and the geometry of the channel through which the fluid is flowing.

Re is a function of the density, ρ, dynamic viscosity, μ, average velocity of the fluid, v, and the characteristic length of the channel in which the fluid is flowing, D, according to the following equation:

$$Re = \frac{\rho D \bar{v}}{\mu}$$

The characteristic length of a fluid flow channel is its width if it is rectangular in cross-section or its diameter if it is circular in cross-section. The average velocity of a fluid in a channel or duct is given by:

$$\bar{v} = \frac{Q}{A}$$

where Q is the volumetric flow rate of the fluid, and A is the cross-sectional area of the fluid flow channel. As a result of the flow being laminar and the depth of the channel being at least as large as the width, the following two dimensional equation for laminar flow velocity profiles can be useful:

$$v(z) = \frac{3}{2}\bar{v}\left(1 - \left(\frac{2z}{h}\right)^2\right)$$

This equation provides the fluid velocity, v, as a function of distance, z, from the centerline of the channel, where h is the total width of the flow channel and, again, is the average fluid flow speed in the channel. Upon examination of this equation, one can see that the velocity profile of a fluid flowing in a channel is parabolic in nature and that it diminishes to zero at the walls of the channel. The fact that velocity diminishes to zero at the wall of a fluid flow channel holds for both laminar and turbulent flows and is referred to as the 'no-slip' condition. Note that that z=0 is defined as the center of the channel and that the flow velocity profile is symmetric about this point. Additionally, we see that vmax occurs at the center of the channel, where the fluid velocity at the center of the channel is defined as $$v(0) = \frac{3}{2}\bar{v} = v_{max}$$

In some implementations, the optimization of fluid flow for maximum antigen detection can be applied to flow channels embedded within a piezoelectric cantilever, such as the sensor 300. An advantage of such a design is the flow cell and sensor are self-contained, and the mechanical vibration of the piezoelectric devices can serve as a pump for recirculating the solution within the cavity.

Figure 3B:
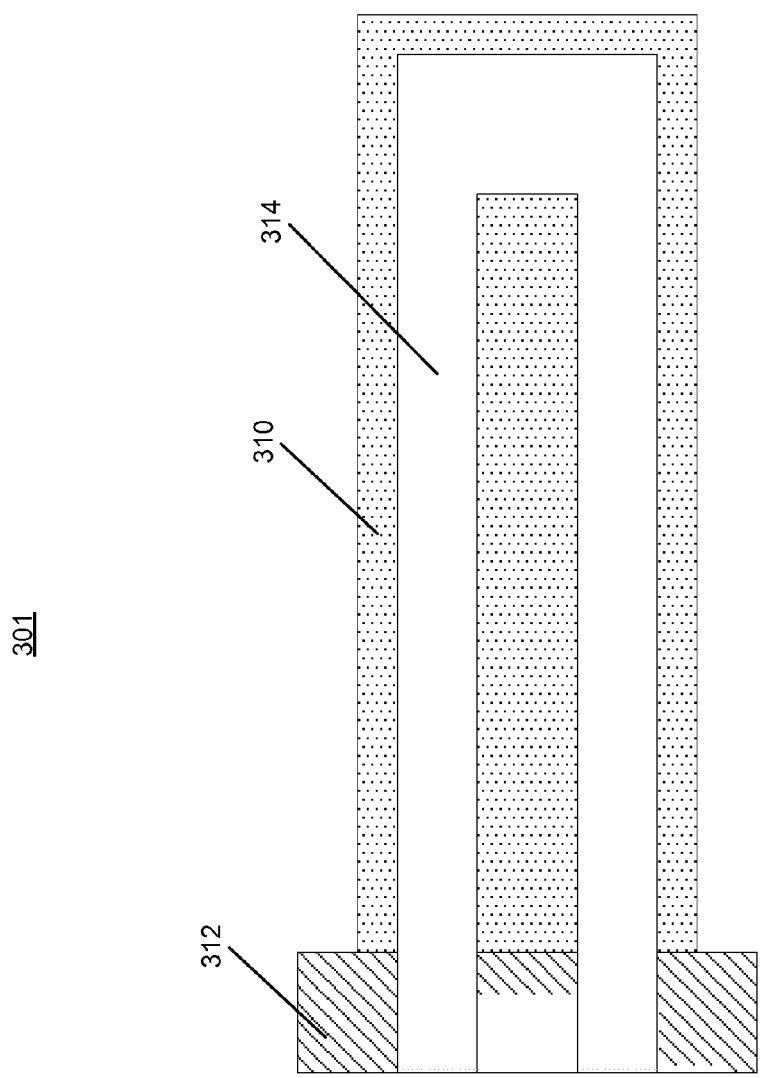
FIG. 3B shows a top cross-sectional view of a piezoelectric cantilever sensor, according to an illustrative implementation.

FIG. 3B shows a top cross-sectional view of a piezoelectric cantilever sensor 301, according to an illustrative implementation. The sensor 301 includes a beam 310 fixed to a clamp 312. A channel 314 is embedded within the beam 310. The channel 314 flows through the clamp 312 as well. In some implementations, the clamp 312 can serve as an inlet and an outlet for the test solution containing the analyte. As solution flows through the channel 314, some of the analyte can bond to the sensor 314, changing its vibrational characteristics. The change can be detected, for example, by measuring changes in the resonant frequency of the sensor 301. Based on the resonant frequency change, it can be determined whether an analyte is present in the solution and, if so, in what concentration.

Figure 3C:
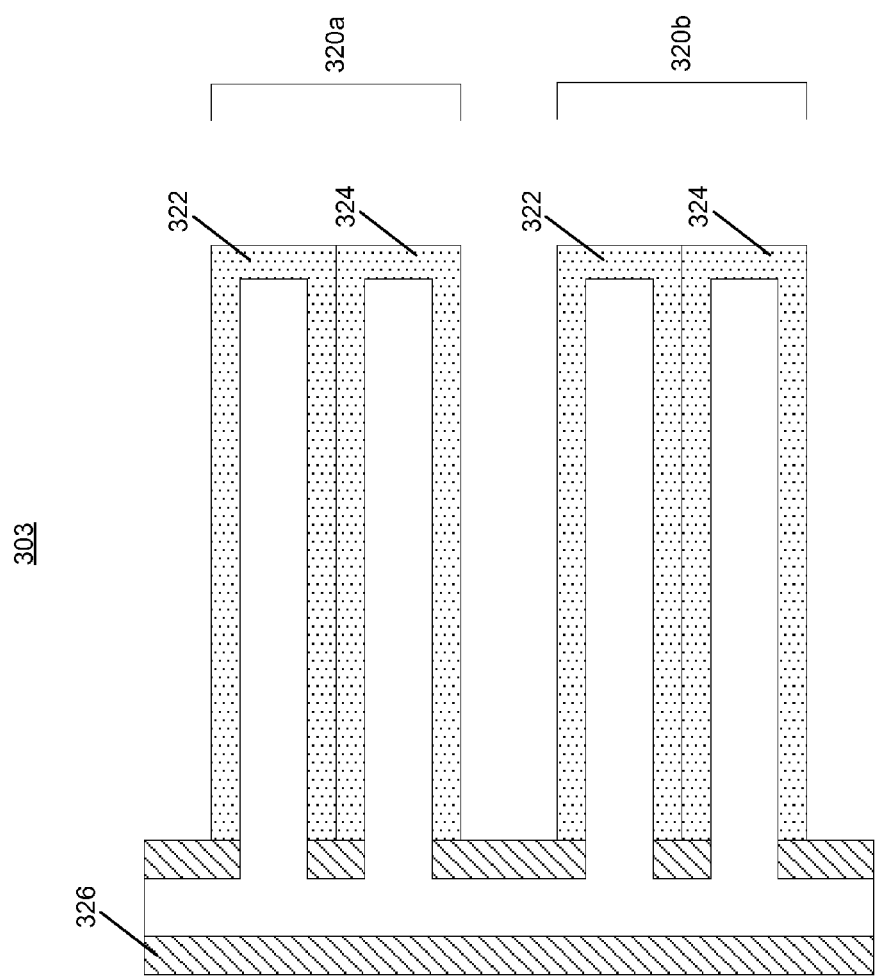
FIG. 3C shows a side cross-sectional view of an array of multilayer piezoelectric sensors, according to an illustrative implementation.
Figure 4:
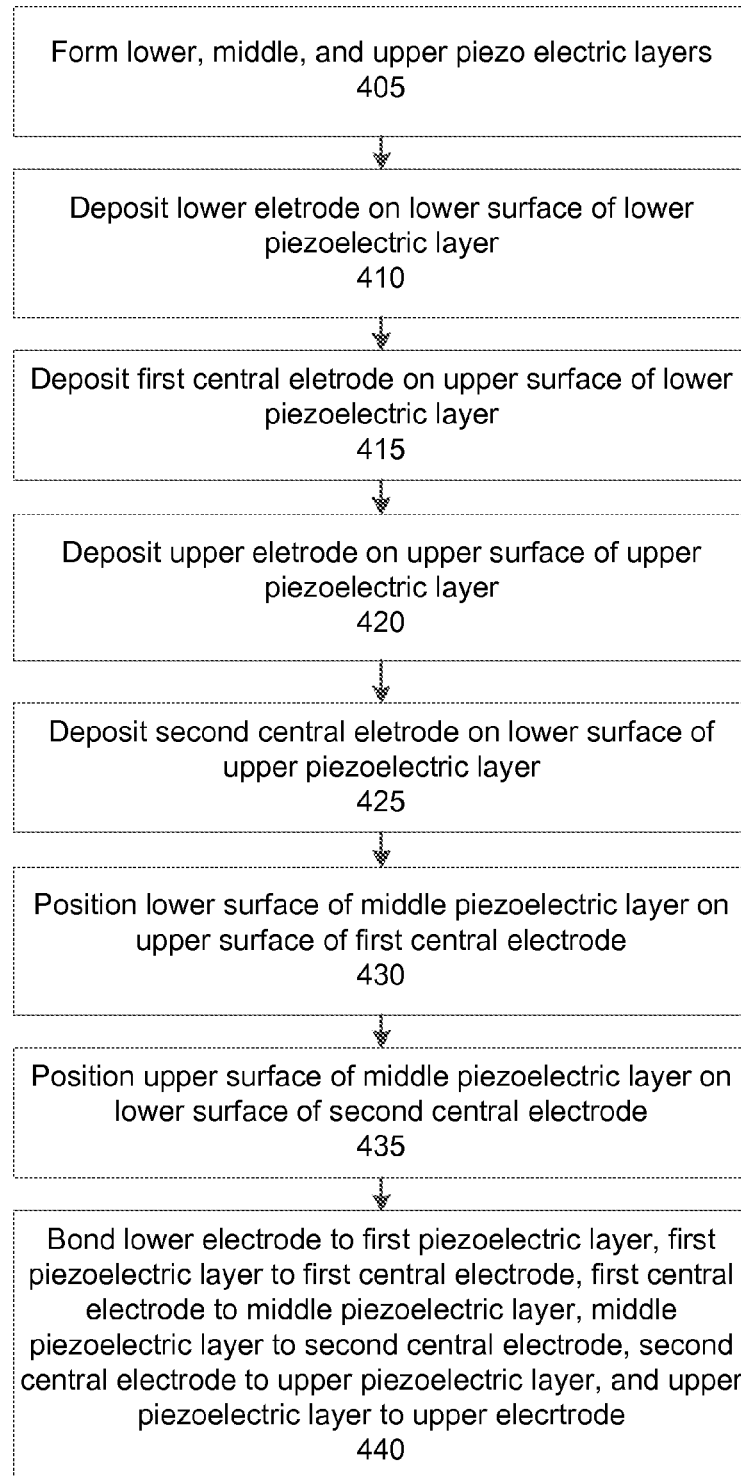
FIG. 4 shows a flow diagram of a process for manufacturing a multilayer piezoelectric device, according to an illustrative implementation.

FIG. 3C shows a side cross-sectional view of an array 303 of multilayer piezoelectric sensors, according to an illustrative implementation. The array includes two piezoelectric sensors 320a and 320b (generally referred to as sensors 320). Each sensor 320 is formed from two piezoelectric layers—an upper layer 322 and a lower layer 324. The sensors 320 are fixed at one end to a clamp 326. An embedded channel 328 is positioned within the sensors 320 and the clamp 326.

In some implementations, the upper layer 322 of each sensor can serve as an experimental sensor while the lower sensor 324 can serve as a control sensor. In some implementations, the sensor 320a can be used to detect a first analyte while the sensor 320b can be used to detect a second analyte. The array 303 can include any number of sensors similar to the sensors 320a and 320b. For example, additional sensors can be included to detect any number of analytes in a single sample of test solution. In other implementations, both sensors 320 can be used to detect the same analyte.

In some implementations, the array 303 can be configured as a biosensor device. For example, the array 303 can be used to detect the presence of cells, parasites, bacteria, viruses or other analytes that may indicate a medical condition in a human patient. To enable detection of these analytes, the sensors 320 can include coatings designed to facilitate binding of the analytes to the surface of the sensors 320. A coating may be configured to attract and bind cells in a fluid sample, thereby changing the vibrational characteristics of the sensors 320.

In some implementations, the test fluid can be a bodily fluid sample taken from a patient. For example, the test fluid introduced into the sensor array 303 can be a blood sample. The patient may be exhibiting symptoms of one or more diseases, and the sensors 320 can be configured to detect a presence or absence of an analyte known to cause the suspected diseases. In other implementations, the test fluid can be a solution into which biological material from a patient or other subject of interest has been introduced.

In some implementations, the sensors 320 of the array 303 may be configured to detect a concentration of a particular analyte, rather than a mere presence or absence. For example, the sensors 320 can exhibit different vibrational responses based on the concentration of an analyte in a test fluid. A coating applied to the surfaces of the sensors 320 can be configured to bind an increased mass of analyte when the test fluid contains an increased concentration of the analyte, relative to the mass of analyte that binds to the sensors 320 when the test solution contains a decreased concentration of the analyte. The resonant frequency of the sensors 320 may change based on the change in their masses. When the array 303 is used as a biosensing device, the ability to determine a concentration of an analyte in a test solution may be more useful than the ability to detect a presence or absence.

In one example, a high white blood cell count may indicate an infection, allergy, or trauma in a patient. Because white blood cells are normally present in a healthy patient as well, merely detecting their presence or absence in a blood sample may not provide useful information to a physician. However, the array 303 can be configured to bind white blood cells to the surface of the sensors 320. The sensors 320 can be configured to change their resonant frequency based on the concentration of white blood cells in the sample fluid. As a result, the array 303 may be used to determine the concentration of white blood cells in a blood sample. This information can then be used by a physician to provide a diagnosis or prescribe treatment.

In some implementations, the array 303 may be used to detect a presence or concentration of several different analytes in a single fluid sample. For example, the array 303 may contain any number of sensors 320. Each sensor may include a different coating configured to bind a particular analyte. Thus, the presence of a first analyte may impact the resonance frequency of one sensor 320, but may not impact the resonance frequency of the other sensors 320. Such a configuration of the array 303 can be used, for example, to determine a particular cause of a symptom exhibited by a patient. A symptom may have several potential causes, each of which is characterized by the presence of a different virus in the blood of the patient. The array 303 can be designed to have at least one sensor configured to detect a presence of these analytes. A blood sample may be introduced into the array 303, and the resulting change in frequency of each sensor 320 may be measured to which analytes are present in the blood sample, thereby facilitating diagnosis by a physician.

In some implementations, other biological analytes may be detected by the sensors 320 of the array 303. For example, the sensors 303 may be configured to bind various proteins, DNA, RNA, sugars, or lipids present in a fluid sample. In some implementations, the fluid sample may be a liquid, such as blood, as discussed above. In other implementations, the fluid sample may be a gas. Particulate matter within the gaseous fluid may be detected by the sensors 320.

In one example, the sensors 320 may be configured to bind spores present in a gas sample. The change in resonant frequency of the sensors 320 can be measured to determine whether the spores are present in the gas sample.

In some implementations, several of the applications for piezoelectric devices described herein may be combined. For example, a piezoelectric energy harvester can be combined with a piezoelectric biosensor to create a self-powered sensor. In one implementation, a self-powered sensor can be used to monitor a water treatment plant for pathogens in the water. The energy harvesting component can be mounted on a vibrating pump within the water treatment plant and can harvest energy from the vibration of the pump, as discussed above. The energy can then be used to power the sensor component, which can be configured to detect one or more pathogens within the water supply. In some implementations, the array 303 can be used to implement the sensor component. Similarly, a piezoelectric energy harvester can be used to power an actuator, such as the assembly 200 shown in FIG. 2A.

FIG. 4 shows a flow diagram of a process 400 for manufacturing a multilayer piezoelectric device, according to an illustrative implementation. In brief overview, the process 400 includes forming a lower piezoelectric layer, a middle piezoelectric layer, and an upper piezoelectric layer (block 405), depositing a lower electrode on a lower surface of the lower piezoelectric layer (block 410), depositing a first central electrode on an upper surface of the lower piezoelectric layer (block 415), depositing an upper electrode on an upper surface of the upper piezoelectric layer (block 420), depositing a second central electrode on a lower surface of the upper piezoelectric layer (block 425), positioning a lower surface of the middle piezoelectric layer on an upper surface of the first central electrode (block 430), positioning an upper surface of the middle piezoelectric layer on a lower surface of the second central electrode (block 435), and bonding the lower electrode to the first piezoelectric layer, the first piezoelectric layer to the first central electrode, the first central electrode to the middle piezoelectric layer, the middle piezoelectric layer to the second central electrode, and the second central electrode to the upper piezoelectric layer, and the upper electrode (block 440).

Referring again to FIG. 4, and in greater detail, the process 400 includes forming a lower piezoelectric layer, a middle piezoelectric layer, and an upper piezoelectric layer (block 405). In some implementations, the piezoelectric layers can be formed from a ceramic material such as PZT, PMN-T, PNN-PZT, NKN, LiNb, or BT. For example, a ceramic powder can be prepared as a slurry and formed into a thin sheets using a technique such as tape casting, slip casting, or roller compaction. Each shin sheet can represent one of the lower piezoelectric layer, the middle piezoelectric layer, and the upper piezoelectric layer.

The process 400 includes depositing a lower electrode on a lower surface of the lower piezoelectric layer (block 410). In some implementations, the lower electrode can be formed from a conductive material, such as platinum, silver-palladium, silver, gold, nickel, copper, or tungsten. The lower electrode can be deposited, for example, by screen printing, stencil printing, lithography, or any other material deposition technique. The process 400 also includes depositing a first central electrode on an upper surface of the lower piezoelectric layer (block 415), depositing an upper electrode on an upper surface of the upper piezoelectric layer (block 420), and depositing a second central electrode on a lower surface of the upper piezoelectric layer (block 425). In some implementations, the first central electrode, second central electrode, and upper electrode can be formed from a conductive material similar to the conductive materials that can be used to form the lower electrode and can be deposited according to similar techniques. In some implementations, the process 400 also can include defining vias within the piezoelectric layers and filling the vias with conductive material to electrically couple one or more of the electrodes to one another. For example, in some implementations, the lower electrode may be electrically coupled to the upper electrodes. Similarly, in some implementations, the first central electrode may be coupled to the second central electrode.

The process 400 includes positioning a lower surface of the middle piezoelectric layer on an upper surface of the first central electrode (block 430) and positioning an upper surface of the middle piezoelectric layer on a lower surface of the second central electrode (block 435). In some implementations, the process 400 can also include defining fiducial markers within the piezoelectric layers of deposited electrodes. Fiducial markers can facilitate alignment of the layers of the multilayer device. In some implementations, the positioning steps (blocks 430 and 435) can include bringing the surfaces of the various layers of the device into contact with one another.

The process 400 includes bonding the lower electrode to the first piezoelectric layer, the first piezoelectric layer to the first central electrode, the first central electrode to the middle piezoelectric layer, the middle piezoelectric layer to the second central electrode, and the second central electrode to the upper piezoelectric layer, and the upper electrode (block 440). In some implementations, the bonding step can be a lamination technique carried out at a temperature in the range of about 20 degrees Celsius to about 300 degrees Celsius. The layers of the piezoelectric device can be bonded to one another all at once. In other implementations, the adjacent layers can be bonded individually to build up the device layer by layer.

In some implementations, the process 400 can also include defining a channel within one or more of the piezoelectric layers. For example, a sacrificial material can be injected into a piezoelectric layer to define a channel. The process 400 can then include a bisque firing step in which the device is subjected to a temperature of about 500 degrees Celsius, which can cause the sacrificial material to break down, leaving the channel embedded within the piezoelectric layer. In some implementations, the process 400 can also include a sintering step to promote densification of the piezoelectric layers and electrodes. For example, the piezoelectric layers and electrodes can be co-sintered after deposition of the electrode material onto the piezoelectric layers. In some implementations, the co-sintering process can be carried out at a temperature in the range of about 600 degrees Celsius to about 1500 degrees Celsius.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A piezoelectric device array, the array comprising:
   a first piezoelectric beam and a second piezoelectric beam each coupled to a clamp and extending substantially perpendicular to the clamp, wherein the piezoelectric beams are configured to oscillate substantially in phase with one another;
   a first proof mass coupled to the first piezoelectric beam; and
   a second proof mass coupled to the second piezoelectric beam, the first and second proof masses selected to enable the first and second piezoelectric beams to oscillate in phase.

2. The piezoelectric device array of claim 1, wherein a surface of the first piezoelectric beam is substantially in contact with a surface of the second piezoelectric beam when the first and second piezoelectric beams are at rest.

3. A piezoelectric sensor comprising:
   a first piezoelectric beam having a first end fixed to a clamp, the first beam comprising a channel embedded within the first beam and configured to transport a test fluid;
   a second piezoelectric beam having a second end fixed to the clamp, the second beam comprising a second channel embedded within the second beam and configured to transport the test fluid, wherein a surface of the first piezoelectric beam is substantially in contact with a surface of the second piezoelectric beam when the first and second piezoelectric beams are at rest.

4. The piezoelectric sensor of claim 3, wherein the first beam is configured to detect a presence of a first analyte within the test fluid and the second beam is configured to detect a presence of a second analyte, different from the first analyte, within the test fluid.

5. The piezoelectric sensor of claim 3, wherein both the first beam and the second beam are configured to detect a presence of a first analyte within the test fluid.

6. A method for manufacturing a multilayer piezoelectric device, the method comprising:
   forming a lower piezoelectric layer, a middle piezoelectric layer, and an upper piezoelectric layer;
   depositing a lower electrode on a lower surface of the lower piezoelectric layer;
   depositing a first central electrode on an upper surface of the lower piezoelectric layer;
   depositing an upper electrode on an upper surface of the upper piezoelectric layer;
   depositing a second central electrode on a lower surface of the upper piezoelectric layer;
   positioning a lower surface of the middle piezoelectric layer on an upper surface of the first central electrode;
   positioning an upper surface of the middle piezoelectric layer on a lower surface of the second central electrode; and
   bonding the lower electrode to the first piezoelectric layer, the first piezoelectric layer to the first central electrode, the first central electrode to the middle piezoelectric layer, the middle piezoelectric layer to the second central electrode, and the second central electrode to the upper piezoelectric layer, and the upper electrode.

7. The method of claim 6, wherein forming the lower piezoelectric layer, the middle piezoelectric layer, and the upper piezoelectric layer comprises:
   preparing a piezoelectric material slurry; and
   tape casting the slurry to form the lower piezoelectric layer, the middle piezoelectric layer, and the upper piezoelectric layer.

8. The method of claim 6, further comprising sintering the lower piezoelectric layer, the middle piezoelectric layer, and the upper piezoelectric layer.

9. The method of claim 6, further comprising forming a channel within one of the lower piezoelectric layer, the middle piezoelectric layer, and the upper piezoelectric layer.

10. The method of claim 6, wherein depositing the lower electrode on the lower surface of the lower piezoelectric layer further comprises screen printing a conductive material onto the lower surface of the lower piezoelectric layer.

* * * * *